United States Patent [19]

Gersh et al.

[11] Patent Number: 4,897,551
[45] Date of Patent: Jan. 30, 1990

[54] LEAK DETECTOR

[75] Inventors: Michael E. Gersh, Bedford; Steven M. Adler-Golden, Newtonville; Neil M. Goldstein, Medford; Fritz Bien, Concord, all of Mass.

[73] Assignee: Spectral Sciences, Inc., Burlington, Mass.

[21] Appl. No.: 179,847

[22] Filed: Apr. 11, 1988

[51] Int. Cl.⁴ .......................................... G01N 21/64
[52] U.S. Cl. ................... 250/461.1; 250/301; 250/458.1
[58] Field of Search ............... 250/461.2, 461.1, 459.1, 250/458.1, 301

[56] References Cited

U.S. PATENT DOCUMENTS

| | | | |
|---|---|---|---|
| 3,783,284 | 1/1974 | McCormack | 250/339 |
| 3,806,727 | 4/1974 | Leonard et al. | 250/301 |
| 3,899,213 | 8/1975 | Fantasia et al. | 250/301 |
| 3,917,945 | 11/1975 | Sema et al. | 250/301 |
| 4,034,219 | 7/1977 | Louden et al. | 250/301 |
| 4,768,513 | 9/1988 | Suzuki | 128/634 |

FOREIGN PATENT DOCUMENTS

| | | | |
|---|---|---|---|
| 2565347 | 12/1985 | France | 250/461.1 |
| 60-213842 | 10/1985 | Japan | 250/301 |

Primary Examiner—Constantine Hannaher
Attorney, Agent, or Firm—Joseph S. Iandiorio; Brian M. Dingman

[57] ABSTRACT

A leak detector for monitoring, in an area being investigated, the presence of a liquid having a characteristic fluorescence spectrum. The leak detector includes a radiation source, with the radiation provided to the area being investigated. The detector also includes a collector for collecting radiation, in the fluorescence emission band of the liquid being monitored, emitted from the area being investigated. The presence of this liquid is sensed by detection of a threshold level of collected radiation. The size of a stain of the liquid relative to the size of the field of view of the collector is then determined.

39 Claims, 4 Drawing Sheets

LEAK DETECTOR

FIELD OF INVENTION

This invention relates to a leak detector and more particularly to a device which detects the presence of a leaking liquid in a remote location and determines the size of a stain of this liquid and its leak rate.

BACKGROUND OF INVENTION

Leak detection, especially detection of jet fuel leaking from aircraft fuel tanks, is a very time-consuming task which is often ineffective in detecting leaks in remote, inaccessible locations. Traditionally, this leak detection is performed manually. The existence of fuel leaks can be initially ascertained by the use of fuel vapor detectors. However, these detectors cannot determine the location of the leak or the leak rate. Thus, if a leak is detected with a fuel vapor detector, the area in which the leak is detected must be visually examined. In empty and accessible aircraft dry bays it is possible to visually locate these leaks and estimate the leak rate by manually measuring the size of a fuel spot after an elapsed period of time. Often, it is necessary to first wipe the existing stain dry and apply a red powder to the leak area to brighten the stain of leaking fuel to assist in detection of the size of the fuel leak stain. If the leak is small, this method may be fairly inaccurate.

Not only is this method time consuming and often inaccurate, it is also ineffective in many circumstances. If the leak is in an inaccessible dry bay area, the bay must be disassembled to allow this visual inspection. Thus, conventional leak detection techniques are very labor intensive and can result in large amounts of unscheduled aircraft downtime.

SUMMARY OF INVENTION

It is therefore an object of this invention to provide a leak detector which is quick and accurate.

It is a further object of this invention to provide a leak detector which can detect leaks in inaccessible, remote locations.

It is a further object of this invention to provide a leak detector which is not dependent on subjective operator judgment for accuracy.

It is a further object of this invention to provide a leak detector which can detect small leaks.

It is a further object of this invention to provide a leak detector which can determine the size of a stain of leaking fluid.

It is a further object of this invention to provide a leak detector which can determine the leak rate of the leaking fluid.

It is a further object of this invention to provide a leak detector which does not require ambient lighting.

It is a further object of this invention to provide a leak detector which also can be used to allow visual examination of an inaccessible, remote location for leak confirmation purposes.

This invention results from the realization that fuel leak detection may be improved considerably by illuminating the area of the leak with ultraviolet radiation and detecting radiation, in the fluorescence emission band of the fuel, emitted from the illuminated fuel leak to detect the presence of leaking fuel and determine the size of a stain of this fuel and its growth rate to indicate the fuel leak rate.

This invention features a leak detector for monitoring, in an area being investigated, the presence of a liquid having a characteristic fluorescence spectrum. The leak detector includes a radiation source, means for providing the radiation from the source to the area being investigated, and means for collecting radiation, in the fluorescence emission band of the liquid being monitored, emitted from this area. In addition there are means, responsive to the means for collecting radiation, for detecting a threshold level of this collected radiation to sense the presence of the liquid and also means, responsive to the means for collecting radiation, for determining the size of a stain of the liquid relative to the size of the field of view of the detector.

Preferably, the means for providing radiation and the means for collecting radiation include fiber optic means. The fiber optic means for collecting the radiation may include means for ascertaining the distance to the area being investigated. This may be accomplished with a range finder or by including a spacer for keeping the end of the fiber optic means at least a known distance from the area being investigated.

In a preferred embodiment, the wavelength of the radiation source is from 200 to 300 nm and the fluorescence emission band of the liquid being monitored is centered at approximately 340 nm. Alternatively, the irradiation wavelength can be chosen as desired, and the fluoresence wavelength detected approximately 100 nm longer.

The leak detector also may include means, responsive to the means for detecting a threshold level of collected radiation, for indicating the presence of the liquid when the threshold level is reached. This level is preferably above the background radiation level. The means for indicating the presence of liquid may be an audio output or flashing light with an intensity or frequency that varies as a function of the intensity of the collected radiation. The means for determining the relative size of the stain may include means for comparing the intensity of the collected radiation to a reference intensity to determine the size of the stain relative to the size of the field of view of the detector. This relative size may be displayed by a meter or digital readout. In addition, there may also be means for viewing the area being investigated. This means for viewing preferably includes fiber optic means for viewing remote locations, and further may include fiber optic means for directing visible light to these locations.

The leak detector may further include means, responsive to the means for collecting radiation, for determining the actual size of a stain of the liquid in the area being investigated. This means for determining the actual size of the stain may include means for resolving the actual size of the area being investigated, and may further include means for comparing the intensity of the collected radiation to a reference intensity. The actual size of the area being investigated may be resolved by including means for determining the distance from the probe to the area being investigated. There may also be a means for indicating the actual size of the stain to an operator.

This leak detector may further include means for determining the leak rate of the liquid. This means for determining the leak rate preferably includes means for calculating the change in the actual size of the stain with time. This may be done by comparing the size of the stain at one time to the previously determined stain size. The previously determined stain size may be accessed by including means for storing the size of the stain at the previous time. There may also be a means for indicating the leak rate to an operator.

Alternatively, the leak detector includes a radiation source, means for providing the radiation from the source to an area being investigated, and means for collecting radiation in the fluorescence emission band of the liquid being monitored emitted from this area. In addition, there are means, responsive to the means for collecting radiation, for determining the amount of the area covered with the liquid to determine the size of a stain of the liquid.

This embodiment preferably includes means, responsive to the means for determining the size of the stain, for indicating the size of the stain to the operator. There may also be included a means for resolving the size of the area being investigated. The means for determining may include means for comparing the intensity of the collected radiation to a reference intensity to determine the size of the stain relative to the resolved size of the area being investigated.

The radiation may be provided to the stain by fiber optic means. The radiation emitted from the stain of liquid may be collected by fiber optic means. There may also be a means for ascertaining the distance from the fiber optic collector to the area being investigated. This may be accomplished by including a range finder or by providing a spacer for keeping the end of the fiber optic means at least a known distance from the surface being investigated. This embodiment may also further include means for determining the leak rate of the liquid. This may be accomplished by including means for calculating the change in size of the stain with time. The leak rate may be reported by some means for indicating the leak rate.

In another alternative embodiment, the leak detector is a leak rate detector for monitoring, in the location being investigated, the presence of a liquid having a characteristic fluorescence spectrum. This leak rate detector includes a radiation source, means for providing the radiation from the source to the location being investigated, and means for collecting radiation in the fluorescence emission band of the liquid being monitored, emitted from a known area of this location. In addition, there are means, responsive to the means for collecting radiation, for determining the amount of the known area covered with liquid to determine the size of the stain of the liquid and also means, responsive to the means for determining the size of the stain, for computing the leak rate of the liquid. The means for computing may include means for calculating the rate of growth of the stain size. This may be accomplished by comparing the size of the stain at one time to the size of the stain at a previous time. There are also preferably means for indicating the leak rate and stain size to the operator.

DISCLOSURE OF PREFERRED EMBODIMENT

Other objects, features and advantages will occur from the following description of a preferred embodiment and the accompanying drawings, in which.

Figure 1:
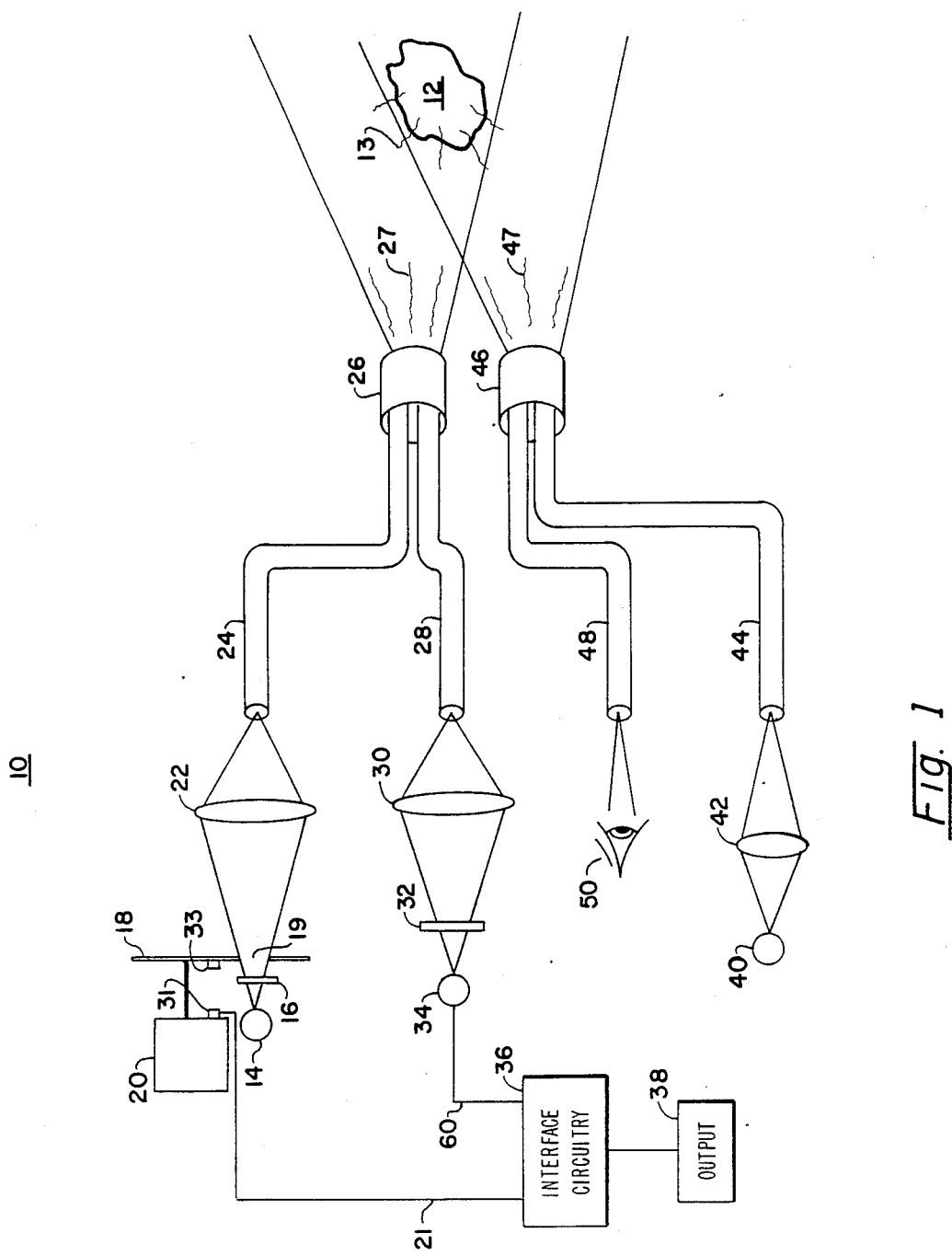
FIG. 1 is a schematic diagram of a leak detector according to this invention.

A leak detector according to this invention may be accomplished by providing a radiation source with a radiation spectrum centered at a known wavelength and delivering this radiation to an area being investigated for a leak. Radiation in the fluorescence emission band of the leaking liquid emitted from the area being investigated is collected. The leak detector is especially useful for detecting jet fuel leaks in remote, inaccessible aircraft dry-bay areas.

Typically, the leak detector is used for monitoring the presence of a liquid having a characteristic fluorescence spectrum in the area being investigated. Preferably, the leak detector is first used to scan an area in which there may be leaking fuel to detect a fuel leak. The detector is then used to search this area to determine the location of the fuel leak. Once the location is determined, the leak detector is used to determine the size of a stain of leaking fuel. If the stain is smaller than the field of view of the leak detector, the leak detector is then used to determine the fuel leak rate. If the fuel stain is larger than the instrument's field of view, the stain is first dried, and then is re-measured to determine the leak rate.

For use as a jet fuel leak detector, the radiation provided to the area being investigated typically has a spectrum centered at from 200 to 300 nm. The fluorescence emission band of the jet fuel is typically centered at approximately 100 nm higher then the incident radiation. For example, the fluoresence band is typically centered at approximately 340 nm for irradiation at 254 nm.

The leak detector preferably includes a detector, responsive to the collected radiation, for detecting a threshold level of the collected radiation to sense the presence of the leaking liquid in the area being investigated. It also preferably includes a device for determining the size of a stain of the leaking liquid relative to the size of the field of view. Preferably, the radiation is provided to and collected and returned from the remote location by a fiber optic bundle. The fiber optic bundle also preferably includes a spacer for keeping its end at least a known distance from the dry-bay surface being investigated. Alternatively, the bundle may include a range finder. Either of these provides a field of view with a known size for stain size and leak rate determination.

In addition, the leak detector preferably includes a way of viewing the area being investigated. This is typically accomplished with a fiber optic bundle which is useful for viewing remote locations. To allow viewing of remote locations that are dark, there may also be a device for providing visible light to the area. This device is typically also a fiber optic bundle.

The leak detector is preferably first used in a search mode. The search is typically performed by scanning the area being investigated from a relatively long distance. When leaking fuel is present in the area being investigated, the fuel is irradiated with the radiation, which causes the fuel to fluoresce. The leak detector then detets a low, threshold level of this fluorescence radiation which is preferably somewhat above the background radiation level. This detection is preferably indicated by an output device such as a light or beeper which alerts the operator to the presence of leaking fuel in the area being investigated. The intensity or frequency of this output may be varied to indicate the intensity of the collected radiation, which is related to the size of the fuel stain relative to the size of the field of view. This allows the operator to "home in" on the leak by directing the search toward the location of the leak. The relative size of the stain may be determined by a device which compares the intensity of the collected radiation to a reference intensity. An output device for displaying this relative size may be included as well.

Once the fuel leak has been detected by this "homing in" search procedure, the leak detector is then used to measure the actual size of the fuel stain. Preferably, this is accomplished by including circuitry for comparing the intensity of the collected radiation to a reference intensity. Preferably, this is accomplished by first resolving the actual size of the area being investigated and then comparing the intensity of collected radiation to the theoretical intensity of radiation which would be collected if the liquid filled the entire field of view of the detector. An output device is further included for indicating the size of the stain to the operator.

Once the leak has been located and the actual size of the stain has been determined, the leak detector is used for determining the fuel leak rate. To accomplish this, the detector includes circuitry for calculating the change in the actual size of the stain with time. This is best accomplished by storing the stain size in memory, and then comparing the next determined stain size to the stored stain size to indicate the rate of growth of the stain. This data is then converted to leak rate data, and the leak rate is then indicated to the operator by an output device such as a digital readout or meter.

There is shown in FIG. 1 a leak detector 10 including a radiation source 14 which is preferably a low-pressure mercury vapor lamp. Radiation from lamp 14 passes through interference filter 16 which preferably passes 254 nm radiation only, and through opening 19 in chopper wheel 18. Motor 20 drives chopper wheel 18 at a predetermined, known rate. Proximity sensor 31 detects location indicator 33 mounted on chopper wheel 18. This proximity sensor provides a reference signal over line 21 to interface circuitry 36 to improve the accuracy of the detector by enabling the detection circuitry only at the times when the lamp radiation passes through the chopper wheel. The filtered radiation from lamp 14 is focused by lens 22 onto the illumination leg 24 of a silica fiber optic bundle. The radiation emerges at probe end 26 as shown at 27, and impinges on fuel leak stain 12. The liquid absorbs the incident radiation and fluoresces at a characteristic wavelength spectrum as shown by lines 13. The strength of this fluorescence radiation is not dependent on the thickness of the fuel leak stain. This fluorescence is collected by the fiber optic bundle and travels down the collection leg 28 of the bundle. On emerging from the probe, the collected radiation is focused by lens 30 through wavelength specific filter 32 onto photomultiplier tube 34. The output of photomultiplier tube 34 is fed over line 60 to interface circuitry 36. Output device 38 is responsive to interface circuitry 36 and indicates detection of a fuel stain, its size, and the fuel leak rate.

The leak detector may further include means for viewing the area being investigated. In this instance, fiber optic bundle 48 is used for human viewing of fuel stain 12, as is diagrammatically depicted by human eye 50. To view dark, inaccessible locations, the leak detector further includes fiber optic bundle 44 for providing visible light 47 to illuminate the area being investigated. Here, light bulb 40 supplies light, which is focused by lens 42 onto fiber optic bundle 44. The light travels through bundle 44 and emerges at probe end 46 to illuminate fuel leak stain 12.

Figure 2:
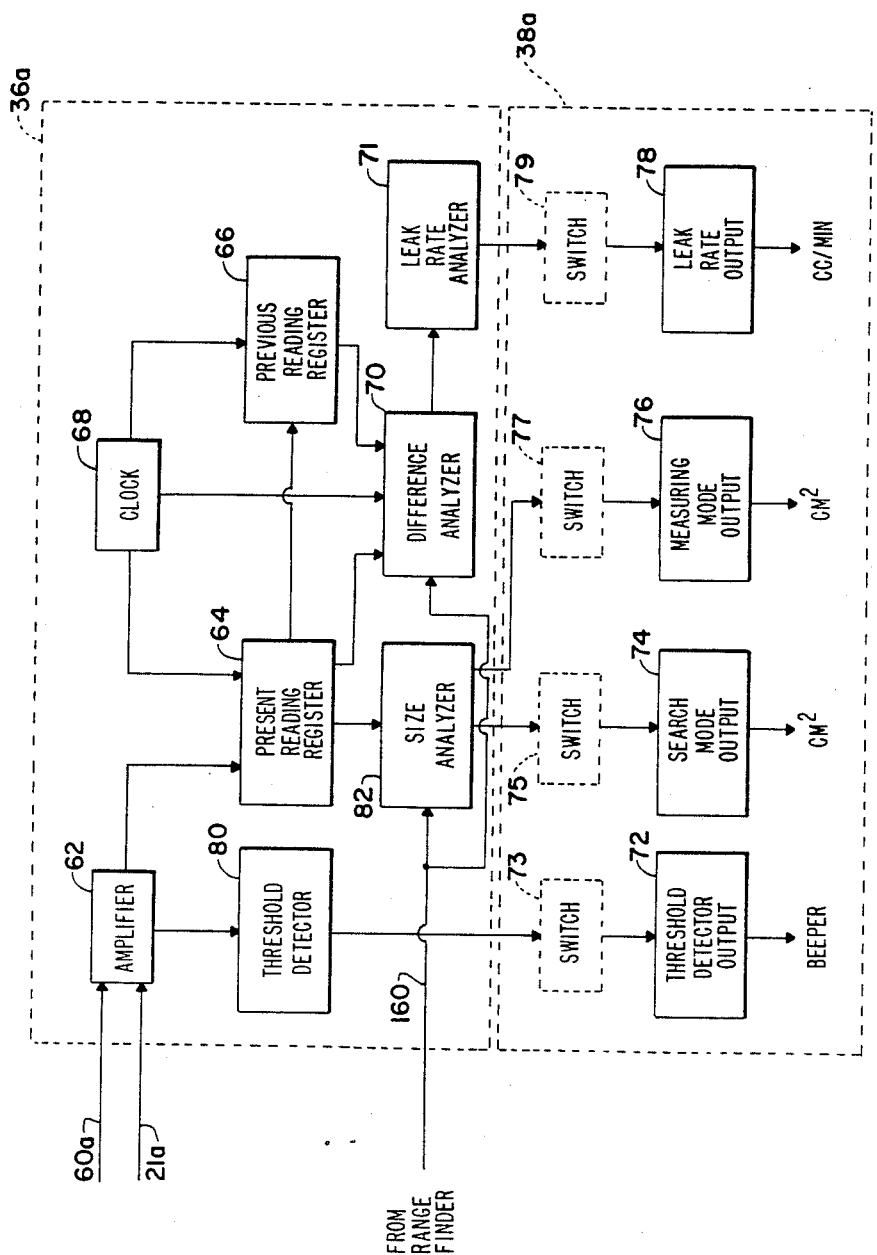
FIG. 2 is a block diagram of the interface circuitry and output devices of the fuel leak detector of FIG. 1.

The interface circuitry, enclosed by dashed line 36a, and output devices, enclosed by dashed line 38a, are shown in detail in FIG. 2. The photomultiplier tube output enters amplifier 62 through line 60a. The reference signal from proximity sensor 31, FIG. 1, enters lock in amplifier 62 through line 21a. Lock in amplifier 62 corrects the fluorescence signal from the fuel stain for ambient light contributions, thereby rejecting all interference from other light sources. The amplifier output is fed to threshold detector 80 and present reading register 64. Threshold detector 80 is preset to pass signals to threshold detector output 72 only when they are above a predetermined level. This level is set slightly above the expected background radiation level, and results in fewer false leak detection indications. Threshold detector output device 72 may be a meter with a deflecting needle or may be some type of audio output or flashing light that alerts the operator to the detection of a leak in the area being investigated.

Signals from amplifier 62 also enter present reading register 64 at times controlled by clock 68. Present reading register 64 stores the present reading of amplifier 62, and then passes this reading to previous reading register 66, size analyzer 82, and difference analyzer 70.

Size analyzer 82 compares the strength of the amplified signal to a reference. This reference is typically equivalent to a full scale reading. That is, it represents the signal which would be generated if the entire field of view were covered with liquid. When the size of the field of view is known, size analyzer 82 can determine the actual stain size. When used in the search mode, however, the size of the stain relative to the size of the field of view is calculated by size analyzer 82 and passed to search mode output 74. This output may be a meter, but is preferably an audio output with an amplitude or frequency which increases as the magnitude of the amplified signal increases to indicate the relative size of the fuel stain detected. This allows an operator to first search out and find a fuel stain, and then home in on the stain to prepare for stain size measurement and fuel leak rate determination.

After a fuel stain has been detected and its location confirmed, the probe tip is moved up to a known distance from the surface with the fuel stain on it. When the probe is a known distance from the surface, the fuel leak detector can be used in its measuring mode. This distance can be determined by including a spacer bar on the end of the probe to keep the probe tip at least a known distance from the surface being investigated, or by employing a range finder proximate the probe tip. The range finder output travels over line 160 to size analyzer 82.

In the measuring mode, size analyzer 82 compares the amplitude of the signal from present reading register 64 to a full-scale amplitude indicative of a stain covering the full field of view of the fuel leak probe, and calculates the size of the fuel stain. Size analyzer 82 determines the full-scale amplitude based on field of view size determination from the distance information from range finder 158, FIG. 3, and the known angle of view of the fiber optic bundle. Measuring mode output 76 indicates the size of the stain and can be either an analog or a digital output. This output indicates the size of the stain of leaking fuel, in, for instance, square centimeters or square inches.

The final mode in which the leak detector is used is the leak rate determination mode. In this mode, the leak detector is continuously calculating the size of the stain. Difference analyzer 70, controlled by clock 68, analyzes the previous reading from previous reading register 66 and the present reading from present reading register 64 and determines the change in fuel leak stain size with time. Analyzer 70 calculates the present and previous fuel stain size the same way that size analyzer 82 does. Difference analyzer 70 receives range information from range finder 158, FIG. 3, over line 160. Alternatively, the distance of the probe tip from the area being investigated can be fixed by including a spacer bar on the probe tip. Since the probe has a known angle of view, the size of the field of view can be calculated. A reference intensity of the maximum collectable radiation from this known area is then compared against the collected radiation intensity to determine fuel stain size.

The output of difference analyzer 70 is passed to leak rate analyzer 71, which converts the stain growth rate information into leak rate information. Leak rate output 78 is responsive to analyzer 71 and again may be an analog or a digital output which reports the leak rate in units of, for instance, ounces or cubic centimeters per minute. Switches 73, 75, 77 and 79, shown in dashed line, may be included to selectively turn on only the output device for the mode being used at a particular time to decrease operator confusion. These switches could also be used to switch scales of a single output meter with four scales, one for use in each of the four modes.

Figure 3:
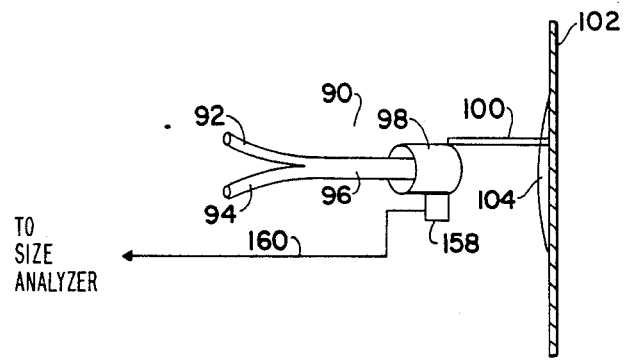
FIG. 3 is a schematic diagram of a leak detector probe tip according to this invention.

A typical probe tip 90 is shown in detail in FIG. 3. Here, fiber optic bundle 96 includes bundle leg 92 for supplying radiation and bundle leg 94 for returning fluorescence radiation detected from stain 104. Ring 98 holds the end of bundle 96 in place and also anchors spacer bar 100, which keeps the end of probe 96 at least a known distance from dry bay surface 102. Spacer 100 is necessary for the instrument to be useful as a leak rate detector because the size of the field of view of probe 96 must be known. Alternatively, the size of the field of view can be determined by employing range finder 158 to determine the distance to dry bay surface 102. Since probe 96 has a known angle of view, the size of the field of view can be determined by, for example, size analyzer 82, FIG. 2.

Figure 4A:
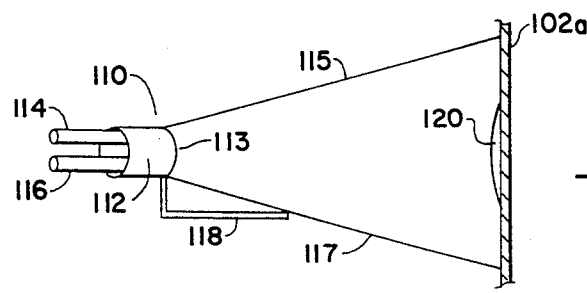
FIG. 4A is a schematic diagram of the leak detector probe being used in the search mode.
Figure 4B:
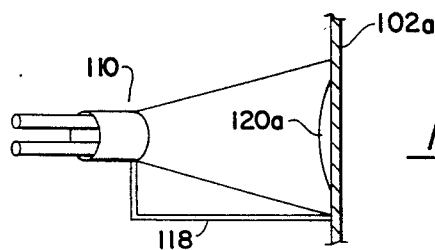
FIG. 4B is a schematic diagram of the probe of FIG. 4A being used in the measuring mode.
Figure 4C:
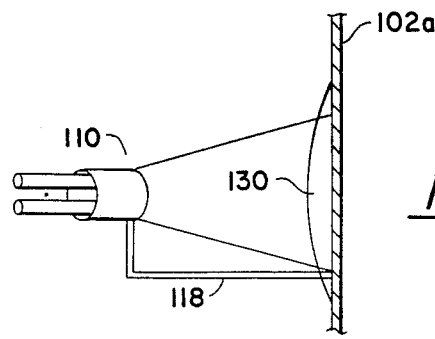
FIG. 4C is a schematic diagram of the probe of FIG. 4B being used to measure a large fuel stain.

FIGS. 4A through 4C show the instrument being used in several of its modes. Probe tip 110, FIG. 4A, is shown being used in the search mode. Here, fiber optic legs 114 and 116 are encompassed by ring 112, which holds spacer bar 118. End 113 of the fiber optic bundle is shown farther from dry bay surface 102a than the predetermined length of spacer bar 118. Thus, in the search mode, the field of view of the probe is not known. However, probe 110 does have a known incident angle of view indicated by lines 115 and 117. As seen, fuel stain 120 will appear smaller than it actually is while the instrument is in the search mode because it takes up only a fraction of the field of view of the probe.

The same probe is shown in the measuring mode in FIG. 4B. Here, probe 110 is held a predetermined, known distance from dry bay 102a by spacer 118. In this mode, the field of view of probe 110 is fixed and known. Thus, stain 120a can be accurately measured by comparing the fluorescence emission collected from stain 120a to the maximum amount of fluorescene emission which would be collected if the stain filled the entire field of view of probe 110.

A condition which can cause erroneous readings is shown in FIG. 4C. Here, fuel stain 130 is larger than the field of view of probe 110. As can be seen, the leak detector is being used in the measuring mode because spacer bar 118 is touching dry bay surface 102a. Since stain 130 completely fills the field of view of probe 110, the measuring mode output will be at its maximum and there will be an uncertainty. The stain could be exactly the maximum size detectable or greater than this size. Thus, a maximum reading is considered as an indication that a stain is too large to measure. To measure the fuel stain size and fuel leak rate in this circumstance, the operator must first dry the stain and then use the instrument to measure the growing stain as shown in FIG. 4B. Alternatively, a probe with a range finder could be used to measure stain 130, as the size of the field of view would be known regardless of distance from dry bay 102a.

Figure 5:
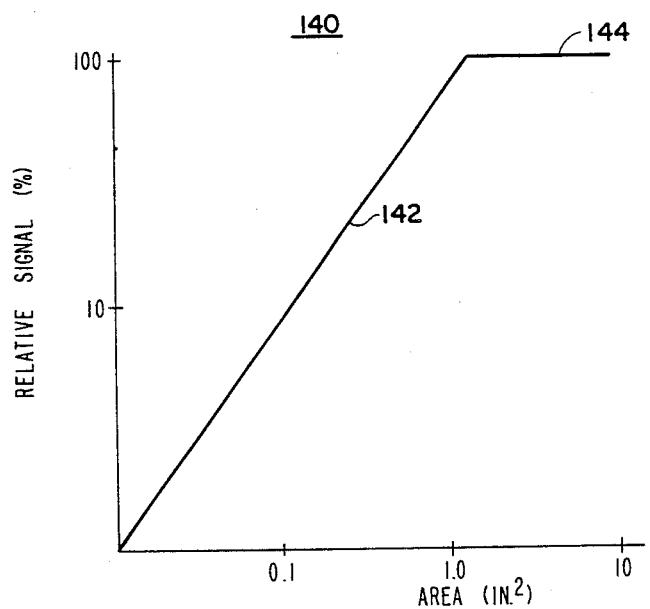
FIG. 5 is a graph of relative signal strength versus fuel stain area.

The response of the instrument and its limitation is shown by graph 140, FIG. 5. Here, fuel stain area in square inches is shown in relation to relative signal strength in percent of full scale. It can be seen that the instrument response is linear with respect to fuel stain area up to a maximum of 1.0 square inches. When the fuel stain is larger than the 1.0 inch field of view of the probe, the instrument output will remain at its maximum. Thus, a maximum output of 100 percent full scale is considered a fuel stain which is too large to be accurately measured.

Figure 6:
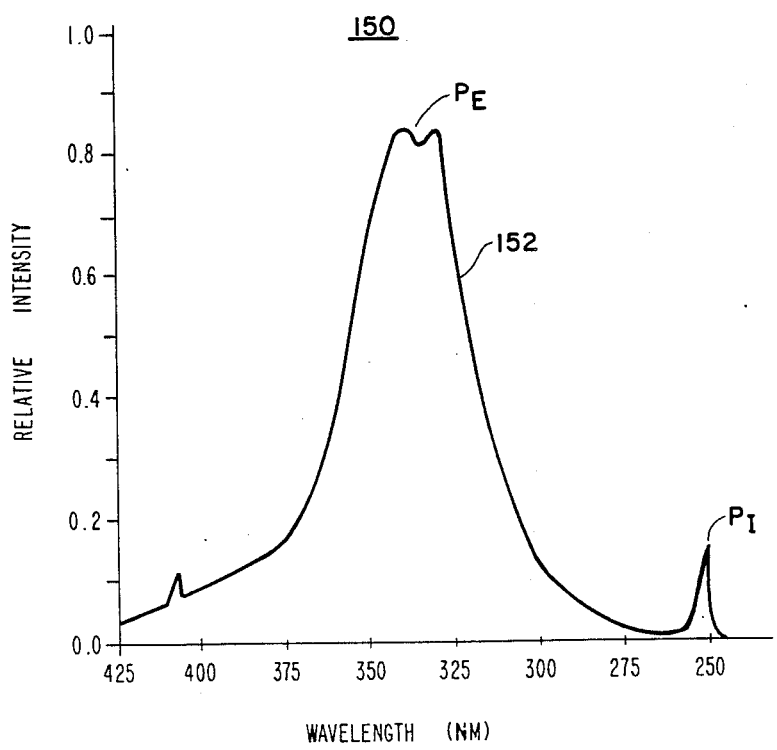
FIG. 6 is a graph of relative intensity of emitted fluorescence radiation versus wavelength for a jet fuel.

The fluorescence spectrum of a typical jet fuel is shown in FIG. 6. Graph 150 is a plot of the relative intensity of collected fluorescence radiation versus wavelength of fluorescence radiation. Graph line 152 includes peaks $P_I$ and $P_E$. $P_I$ is a peak at 254 nm which is the wavelength of incident radiation from the mercury vapor lamp. This peak indicates reflected radiation and can be ignored. The fluorescence radiation from the jet fuel dramatically increases around a wavelength of approximately 340 nm. Thus, by centering the detector response at approximately this wavelength, the fuel leak detector is most accurate. It can also be seen that by including a relatively narrow wavelength detection band of, for instance, from approximately 300 to 400 nm, almost all of the fluorescence radiation emitted from the jet fuel is detected.

Although specific features of the invention are shown in some drawings and not others, this is for convenience only as each feature may be combined with any or all of the other features in accordance with the invention.

Other embodiments will occur to those skilled in the art and are within the following claims:

What is claimed is:

1. A leak detector for monitoring, in an area being investigated, the presence of a liquid having a characteristic fluorescence spectrum, comprising:
   a radiation source;
   means for providing the radiation from said source to said area being investigated;
   means for collecting radiation, in the fluorescence emission band of said liquid being monitored, emitted from said area being investigated;

means, responsive to said means for collecting, for
detecting a threshold level of said collected radiation to sense the presence of said liquid;

means, responsive to said means for collecting, for determining the size of the stain of said liquid relative to the size of the field of view of said means for collecting radiation;

means for determining the distance from said means for collecting radiation to said area being investigated; and means, responsive to said means for determining the size of a stain relative to the field of view and responsive to said means for determining the distance, for resolving the actual size of said stain.

2. The leak detector of claim 1 further including means, responsive to said means for detecting, for indicating the presence of said liquid in said area being investigated when said threshold level is reached.

3. The leak detector of claim 2 in which said threshold level is above the background radiation level.

4. The leak detector of claim 2 in which said means for indicating produces an audio output whose intensity varies as a function of the intensity of said collected radiation.

5. The leak detector of claim 2 in which said means for indicating produces an audio output whose frequency varies as a function of the intensity of said collected radiation.

6. The leak detector of claim 2 in which said means for indicating produces a flashing light whose flashing frequency varies as a function of the intensity of said collected radiation.

7. The leak detector of claim 1 in which said means for determining the size of a stain relative to the field of view includes means for comparing the intensity of said collected radiation to a reference intensity to determine the size of the stain relative to the size of the field of view.

8. The leak detector of claim 1 further including means for displaying the relative size of said stain.

9. The leak detector of claim 1 in which said means for determining the actual size of a stain further includes means for comparing the intensity of the collected radiation to a reference intensity.

10. The leak detector of claim 1 further including means for indicating the actual size of said stain.

11. The leak detector of claim 1 in which said means for providing includes fiber optic means.

12. The leak detector of claim 1 in which said means for collecting includes fiber optic means.

13. The leak detector of claim 12 further including means for ascertaining the distance from said fiber optic means to said area being investigated.

14. The leak detector of claim 13 in which said means for ascertaining includes a range finder.

15. The leak detector of claim 13 in which said means for ascertaining includes a spacer for keeping an end of said fiber optic means at least a known distance from said area being investigated.

16. The leak detector of claim 1 in which the radiation from said source has a wavelength of from 200–300 nm.

17. The leak detector of claim 1 in which said fluorescence emission band is centered at approximately 340 nm.

18. The leak detector of claim 1 further including means for viewing said area being investigated.

19. The leak detector of claim 18 in which said means for viewing includes fiber optic means.

20. The leak detector of claim 18 further including means for providing visible light to said area being investigated.

21. The leak detector of claim 20 in which said means for providing visible light includes fiber optic means.

22. A leak detector for monitoring, in an area being investigated, the presence of a liquid having a characteristic fluorescence spectrum, comprising:
a radiation source;
means for providing the radiation from said source to said area being investigated;
means for collecting radiation, in the fluorescence emission band of said liquid being monitored, emitted from said area being investigated;
means, responsive to said means for collecting, for determining the amount of said area being investigated covered with said liquid to determine the relative size of a stain of said liquid;
means for ascertaining the distance from said means for collecting to said area being investigated; and
means, responsive to said means for determining and to said means for ascertaining, for resolving the size of said area being investigated.

23. The leak detector of claim 22 in which said means for providing includes fiber optic means.

24. The leak detector of claim 22 in which said means for collecting includes fiber optic means.

25. The leak detector of claim 22 in which said means for ascertaining includes a spacer for keeping the end of said fiber optic means at least a known distance from said area being investigated.

26. The leak detector of claim 22 further including means for indicating the size of said stain.

27. A leak detector for monitoring, in an area being investigated, the presence of a liquid having a characteristic fluorescence spectrum, comprising:
a radiation source;
means for providing the radiation from said source to said area being investigated;
means for collecting radiation, in the fluorescence emission band of said liquid being monitored, emitted from said area being investigated;
means, responsive to said means for collecting, for detecting a threshold level of said collection radiation to sense the presence of said liquid;
means, responsive to said means for collecting, for determining the size of a stain of said liquid relative to the size of the field of view of said means for collecting radiation;
means, responsive to said means for collecting, for determining the actual size of a stain of said liquid in said area being investigated; and
means, responsive to said means for determining the size of a stain, for determining the leak rate of said liquid.

28. The leak detector of claim 27 in which said means for determining the leak rate includes means for calculating the change in actual size of said stain with time.

29. The leak detector of claim 28 in which said means for calculating includes means for comparing the actual size of said stain at one time to the actual size of said stain at a previous time.

30. The leak detector of claim 29 further including means for storing the actual size of said stain at the previous time.

31. The leak detector of claim 27 further including means for indicating said leak rate.

32. A leak detector for monitoring, in an area being investigated, the presence of a liquid having a characteristic fluorescence spectrum, comprising:
- a radiation source;
- means for providing the radiation from said source to said area being investigated;
- means for collecting radiation, in the fluorescence emission band of said liquid being monitored, emitted from said area being investigated;
- means, responsive to said means for collecting, for determining the amount of said area being investigated covered with said liquid to determine the size of a stain of said liquid; and
- means for determining the leak rate of said liquid.

33. The leak detector of claim 32 in which said means for determining the leak rate includes means for calculating the change in size of said stain with time.

34. The leak detector of claim 32 further including means for indicating said leak rate.

35. A leak rate detector for monitoring, in a location being investigated, the presence of a liquid having a characteristic fluorescence spectrum, comprising:
- a radiation source;
- means for providing the radiation from said source to said location being investigated;
- means for collecting radiation, in the fluorescence emission band of said liquid being monitored, emitted from a known area of said location being investigated;
- means, responsive to said means for collecting, for determining the amount of said known area covered with said liquid to determine the size of a stain of said liquid; and
- means, responsive to said means for determining, for computing the leak rate of said liquid.

36. The leak rate detector of claim 35 in which said means for computing the leak rate of said liquid includes means for calculating the rate of growth of the size of said stain.

37. The leak rate detector of claim 36 in which said means for calculating the rate of growth includes means for comparing the size of said stain at one time to the size of said stain at a previous time.

38. The leak rate detector of claim 35 further including means for indicating said leak rate.

39. The leak rate detector of claim 35 further including means for indicating the size of said stain.

* * * * *